United States Patent [19]

Rizkalla

[11] 4,354,036

[45] Oct. 12, 1982

[54] PREPARATION OF CARBOXYLIC ACID ESTERS

[75] Inventor: Nabil Rizkalla, River Vale, N.J.

[73] Assignee: The Halcon SD Group, Inc., New York, N.Y.

[21] Appl. No.: 267,974

[22] Filed: May 28, 1981

Related U.S. Application Data

[63] Continuation-in-part of Ser. No. 219,786, Dec. 24, 1980.

[51] Int. Cl.³ ............................................. C07C 67/38
[52] U.S. Cl. ............................. 560/233; 260/410.9 R; 560/100; 560/101; 560/105; 560/114
[58] Field of Search ............... 560/233, 114, 105, 100, 560/101; 260/410.9 R

[56] References Cited

U.S. PATENT DOCUMENTS

| | | | |
|---|---|---|---|
| 2,689,261 | 9/1954 | Reppe | 560/233 |
| 2,768,968 | 10/1956 | Reppe | 560/233 |
| 2,771,478 | 11/1956 | Reppe | 560/233 |
| 3,505,394 | 4/1970 | Olivier | 560/233 |
| 4,179,403 | 12/1979 | Kim | 560/233 |

FOREIGN PATENT DOCUMENTS

| | | | |
|---|---|---|---|
| 651853 | 4/1951 | United Kingdom | 560/233 |
| 754877 | 8/1956 | United Kingdom | 560/233 |

*Primary Examiner*—Michael L. Shippen
*Attorney, Agent, or Firm*—William C. Long; Riggs T. Stewart; Harold N. Wells

[57] ABSTRACT

A carboxylic acid ester, such as methyl propionate, is prepared by carbonylation of an olefin, such as ethylene in the presence of an alcohol by the use of a molybdenum-nickel or tungsten-nickel co-catalyst in the presence of a promoter comprising an organo-phosphorus compound or an organo-nitrogen compound wherein the phosphorus and nitrogen are trivalent and in the presence of a halide.

4 Claims, No Drawings

PREPARATION OF CARBOXYLIC ACID ESTERS

REFERENCE TO RELATED APPLICATION

This is a continuation-in-part of co-pending application Ser. No. 219,786 filed Dec. 24, 1980.

This invention relates to the preparation of carboxylic acid esters, more particularly mono-carboxylic acid esters, and especially lower alkanoic acid esters, such as propionic acid esters, by the carbonylation of olefins in the presence of an alcohol.

Carboxylic acid esters have been known as industrial chemicals for many years and large amounts are used in the manufacture of various products. Producing carboxylic acid esters by the action of carbon monoxide upon olefins (carbonylation) has been described. In various patents by processes involving several types of catalysts. For example, Slaugh U.S. Pat. No. 3,168,553 shows the reaction of carbon monoxide with an olefinic hydrocarbon in the presence of alcohols by using a Group VIIIb transition metal carbonyl catalyst which contains cobalt, ruthenium, rhodium or iridium in complex combination with carbon monoxide and a trialkyl phosphorus. Anderson et al. U.S. Pat. No. 3,040,090 reacts carbon monoxide and ethylenically-unreacted compound and an alcohol in the presence of a Group VIII noble metal chelate. Morris et al. U.S. Pat. No. 3,917,677 also shows a process involving a reaction among carbon monoxide, ethylenically-unreacted compounds and alcohols which is characterized by using a catalyst containing a rhodium component and a tertiary organo-phosphorus component. This patent contains a discussion of the prior art and the limitations of the prior art procedures, particularly, the poor yields obtainable with them. Furthermore, the prior art process, in general, require relatively high pressures. Even though improved yields are apparently obtained by the process of U.S. Pat. No. 3,917,677, that process requires the use of a very expensive Group VIII noble metal catalyst, i.e., a rhodium catalyst.

It is accordingly an object of the present invention to provide an improved process for the manufacture of carboxylic acid esters, especially lower alkanoic acid esters, such as propionic acid esters, e.g., methyl propionate, which requires neither high pressures nor Group VIII noble metals and makes possible the production of carboxylic acid esters in high yields in short reaction times.

In accordance with the invention, carbonylation of an olefin is carried out by using a molybdenum-nickel or a tungsten-nickel co-catalyst in the presence of a promoter comprising an organo-phosphorus compound or an organo-nitrogen compound wherein the phosphorus and nitrogen are trivalent, and in the presence of an alcohol and an iodide. The surprising discovery has been made that this co-catalyst in combination with the promoter-iodide system of the character indicated makes possible carbonylation of olefins not only at relatively low pressures but with rapid, high yield production of carboxylic acid esters.

Thus, in accordance with the invention, carbon monoxide is reacted with an olefin such as a lower alkene in the presence of an alcohol, e.g., methanol, to produce a carboxylic acid ester, such as a lower alkanoic acid ester, e.g., methyl propionate, the carbonylation taking place in the presence of a halide, e.g., a hydrocarbyl halide, especially a lower alkyl halide, such as ethyl iodide, and in the presence of the co-catalyst and promoter combination which has been identified above. Propionic acid esters, for example, can be effectively prepared in a representative case by subjecting ethylene to carbonylation in the presence of alcohols.

In like manner, esters of other carboxylic acids can be produced by carbonylating the corresponding alkene in the presence of an alcohol.

The reactant olefin may be any ethylenically unsaturated hydrocarbon having from 2 to about 25 carbon atoms, preferably from 2 to about 15 carbon atoms. The ethylenically unsaturated compound has the following general structure:

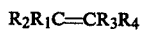

wherein $R_1$, $R_2$, $R_3$ and $R_4$ are hydrogen or the same or different alkyl, cycloalkyl, aryl, alkaryl, aralkyl or wherein one of said $R_1$ and $R_2$ and one of said $R_3$ and $R_4$ together form a single alkylene group having from 2 to about 8 carbon atoms. $R_1$, $R_2$, $R_3$ and $R_4$ can be branched and can be substituted with substituents which are inert in the reactions of the invention.

Examples of useful ethylenically unsaturated hydrocarbons are ethylene, propylene, butene-1, butene-2, 2-methylbutene-1, cyclobutene, hexene-1, hexene-2, cyclohexene, 3-ethylhexene-1, isobutylene, octene-1,2-methylhexene-1, ethylcyclohexene, decene-1, cycloheptene, cyclooctene, cyclononene, 3,3-dimethylnonene-1, dodecene-1, undecene-3, 6-propyldecene-1, tetradecene-2, 3-amyldecene-1, etc., hexadecene-1, 4-ethyltridecene-1, octadecene-1, 5,5-dipropyldodecene-1, vinylcyclohexane, allylcyclohexane, styrene, p-methylstyrene, alpha-methylstyrene, p-vinylcumene, beta-vinylnaphthalene, 1,1-diphenylethylene, allylbenzene, 6-phenylhexene-1, 1,3-diphenylbutene-1, 3-benzylheptene-1, divinylbenzene, 1-allyl-3-vinylbenzene, etc. Of the olefins referred to above, the alpha hydrocarbon olefins and olefins having 2 to about 10 carbon atoms are preferred, e.g., ethylene, propylene, butene-1, hexene-1, heptene-1, octene-1, and the like, i.e., wherein $R_1$, $R_2$, $R_3$ and $R_4$ are hydrogen or alkyl groups totalling 1-8 carbon atoms, preferably the lower alkenes, i.e., alkenes of 2 to 6 carbon atoms, especially ethylene.

The reactant alcohol may be in general any alcohol having the formula ROH, wherein R is alkyl, cycloalkyl, aryl, alkaryl or aralkyl or mixtures thereof; preferably R has 1 to about 18 carbons and most preferably R is alkyl having 1 to about 12 carbons, e.g., methyl, ethyl, propyl, butyl, isobutyl, pentyl, hexyl, nonyl, and the like, or is aralkyl with 7 to about 14 carbons, e.g., benzyl, phenethyl, and the like.

Examples of suitable alcohols include methanol, ethanol, propanol, isopropanol, butanol, tertiary butanol, pentanol, hexanol, 2-ethylhexanol, octanol, decanol, 6-pentadecanol, cyclopentanol, methylcyclopentanol, cyclohexanol, benzyl alcohol, alpha alpha-dimethyl benzyl alcohol, alpha-ethylphenethyl alcohol, naphthyl carbinol, xylyl carbinol, tolyl carbinol, and the like.

In the most preferred embodiment of the invention, carbon monoxide is reacted with ethylene and methanol in the presence of the co-catalyst-promoter-halide system of the character described above to produce methyl propionate in a reaction which may be expressed as follows:

The reaction is preferably carried out in the liquid phase. Carbon monoxide is removed in the vapor phase along with unreacted olefin when the olefin is normally gaseous, e.g., ethylene, and, if desired, recycled. Normally liquid and relatively volatile components such as alkyl halide, normally-liquid unreacted olefin and the alcohol, and any by-products, present in the final product mixture can be readily removed and separated from each other and from the catalyst components as by distillation, for recycling. The net yield of product is substantially exclusively the desired carboxylic acid ester. Most preferably the liquid phase reaction is carried out under boiling conditions and all volatile components are removed in the vapor phase, leaving the catalyst in the reactor. The reaction is suitably carried out in a reaction zone to which the carbon monoxide, the olefin, the alcohol, the halide, the co-catalyst and the promoter are fed.

As will be apparent from the foregoing equation, a carbonylation reaction of the character described selective to a carboxylic acid ester requires at least one mol of carbon monoxide and one mol of alcohol per mol (equivalent) of ethylenically-unsaturated linkage reacted.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under superatmospheric pressure but, as previously mentioned, it is a feature of the invention that excessively high pressures, which require special high-pressure equipment, are not necessary. In general, the reaction is effectively carried out by employing a carbon monoxide partial pressure which is preferably at least 15 but less than 2,000 psi, most preferably 15 to 1,000 psi and particularly 30 to 200 psi, although CO partial pressures of 1 to 5,000 or even up to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that required to maintain the liquid phase and, in this case, the reaction can be advantageously carried out in an autoclave or similar apparatus. At the end of the desired residence time the reaction mixture is separated into its several constituents, as by distillation. Preferably, the reaction product is introduced into a distillation zone which may be a fractional distillation column, or a series of columns, effective to separate the volatile components from the product ester and to separate the product ester from the less volatile catalyst and promoter components of the reaction mixture. The boiling points of the volatile components are sufficiently far apart that their separation by conventional distillation presents no particular problem. Likewise, the higher-boiling organic components can be readily distilled away from the metal catalyst components and any organic promoter which may be in the form of a relatively non-volatile complex. The thus recovered co-catalyst as well as promoter, including the halide component, and unreacted alcohol, can then be combined with fresh amounts of olefin, carbon monoxide and alcohol and reacted to produce additional quantities of carboxylic acid ester. When the reaction is run under boiling conditions, the effluent is entirely in the vapor phase and, after condensation, the components can be separated from each other as described above.

Although not necessary, the process can be carried out in the presence of a solvent or diluent. The presence of a solvent or diluent, preferably the product ester or its acid, e.g., methyl propionate or propionic acid in the case of ethylene carbonylation, will make it possible to employ more moderate total pressures. Alternatively, the solvent or diluent may be any organic solvent which is inert in the environment of the process such as hydrocarbons, e.g., octane, benzene, toluene, xylene and tetralin, or carboxylic acids. A carboxylic acid, if used, should preferably correspond to the ester being produced since, it is preferred that the solvent be one that is indigenous to the system, e.g., propionic acid in the case of ethylene carbonylation, although other carboxylic acids such as acetic acid can also be used. A solvent or diluent, when not the product itself, is suitably selected which has a boiling point sufficiently different from the desired product in the reaction mixture so that it can be readily separated. It is preferred to add the alcohol gradually to the reaction zone to minimize by-product formation. In this case, a solvent is desired and preferably it is one that is indigenous to the system, such as propionic acid or methyl propionate in the case of ethylene carbonylation. Mixtures can be used.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. Hydrogen which may be present as an impurity is not objectionable and even may tend to stabilize the catalyst. Indeed, in order to obtain low CO partial pressures the CO fed may be diluted with hydrogen or any inert gas such as those mentioned above.

The co-catalyst components can be employed in any convenient form, viz., in the zero valent state or in any higher valent form. For example, the nickel and the molybdenum or tungsten can be the metals themselves in finely divided form, or a compound, both organic or inorganic, which is effective to introduce the co-catalyst components into the reaction system. Thus, typical compounds include the carbonate, oxide, hydroxide, bromide, iodide, chloride, oxyhalide, hydride, lower alkoxide (methoxide), phenoxide, or Mo, W or Ni carboxylates wherein the carboxylate ion is derived from an alkanoic acid of 1 to 20 carbon atoms such as acetates, butyrates, decanoates, laurates, benzoates, and the like. Similarly, complexes of any of the co-catalyst components can be employed, e.g., carbonyls and metal alkyls as well as chelates, association compounds and enol salts. Examples of other complexes include bis-(triphenylphosphine) nickel dicarbonyl, tricyclopentadienyl trinickel dicarbonyl, tetrakis (triphenylphosphite) nickel, and corresponding complexes of the other components, such as molybdenum hexacarbonyl and tungsten hexacarbonyl. Included among the catalyst components listed above are complexes of the metal co-catalyst components with organic promoter ligands derived from the organic promoters hereinafter described.

Particularly preferred are the elemental forms, compounds which are halides, especially iodides, and organic salts, e.g., salts of the monocarboxylic acid corresponding to the ester being produced. It will be understood that the foregoing compounds and complexes are merely illustrative of suitable forms of the severl co-catalyst components and are not intended to be limiting.

The specified co-catalyst components employed may contain impurities normally associated with the commercially available metal or metal compounds and need not be purified further.

The organo-phosphorus promoter is preferably a phosphine, e.g. of the formula

wherein $R^1$, $R^2$ and $R^3$ may be the same or different, and are alkyl, cycloalkyl, aryl groups, amide groups, e.g., hexamethyl phosphorus triamide, or halogen atoms, preferably containing 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine. Preferably the organo-nitrogen promoter is a tertiary amine or a polyfunctional nitrogen-containing compound, such as an amide, a hydroxy amine, a keto amine, a di-, tri and other polyamine or a nitrogen-containing compound which comprises two or more other functional groups. Typical organo-nitrogen promoters include 2-hydroxypyridine, 8-quinolinol, 1-methylpyrrolidinone, 2-imidazolidone, N,N-dimethylacetamide, dicyclohexylacetamide, dicyclohexylmethylamine, 2,6-diaminopyridine, 2-quinolinol, N,N-diethyltoluamide, imidazole, pyridine, picolines and the like.

Although generally the organic promoter is added separately to the catalyst system, it is also possible to add it as a complex with any of the co-catalyst metals, such as bis(triphenylphosphine) nickel dicarbonyl and tetrakis (triphenyl phosphite) nickel. Both free organic promoters and complexed promoters can also be used. When a complex of the organic promoter and the co-catalyst metal is used, free organic promoter can also be added.

The amount of each co-catalyst component employed is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, each catalyst component is employed in the amount of 1 millimol to 1 mol per liter of reaction mixture, preferably 5 millimols to 500 millimols per liter and most preferably 15 millimols to 150 millimols per liter.

The ratio of nickel to its co-catalyst component can vary. Typically, it is one mol of nickel per 0.01 to 100 mols of the other co-catalyst component, preferably the nickel component is used in the amount of 1 mol per 0.1 to 20 mols, most preferably 1 mol per 1 to 10 mols of the other co-catalyst component.

The quantity of organic promoter can also vary widely but typically it is used in the amount of 1 mol per 0.1 to 10 mols of co-catalyst components, preferably 1 mol per 0.5 to 5 mol, most preferably 1 mol per 1 to 5 mols of co-catalyst components.

As previously mentioned, in the working up of the reaction mixtures, e.g., by distillation, the promoter components can be readily recovered and recycled to the reaction. The nickel and co-catalyst metal generally remain as the least volatile components, and are recycled or otherwise handled together. They may, however, distill with the volatile components, e.g., in the case of nickel carbonyl. The same is true of the promoter components.

The amount of halide component may also vary widely but, in general, it should be present in an amount of at least 0.1 mol (expressed as elemental halogen) per mol of nickel. Typically, there are used 1 to 100 mols of the halide per mol of nickel, preferably 2 to 50 mols per mol. Ordinarily, more than 1200 mols of halide per mol of nickel are not used.

As previously mentioned, the catalyst system of this invention comprises an organic promoter component, an iodide component and a molybdenum-nickel or tungsten-nickel co-catalyst component. The catalyst system of this invention permits the production of carboxylic ester in high yields in short reaction times without the use of Group VIII noble metals and the presence of the molybdenum or tungsten makes possible good results with relatively small amounts of co-catalyst component and reduced quantities of nickel.

A particular embodiment of the catalyst comprising the molybdenum-nickel or tungsten-nickel co-catalyst component, the organic promoter component and the halide component can be represented by the following formula X:T:Z:Q, wherein X is molybdenum or tungsten, T is nickel, X and T being in zero valent form or in the form of a halide, an oxide, a carboxylate of 1 to 20 carbon atoms, a carbonyl or an hydride; Z is a halide source which is hydrogen halide, halogen, an alkyl halide wherein the alkyl group contains 1 to 20 carbon atoms or an alkali metal halide, and Q is an organo-phosphorus compound or an organo-nitrogen compound wherein the phosphorus and the nitrogen are trivalent. Preferred are the nitrogen and phosphorus compounds previously indicated as being preferably used and in the most preferred form Q is a phosphine of the formula

as hereinbefore defined, especially hydrocarbyl phosphines, the molar ratio of X to T being 0.1–10:1, the molar ratio of X+T to Q being 0.05–20:1 and the molar ratio of Z to X+T being 1–1,000:1, preferably 5–100:1. The halide is chloride, bromide or iodide, preferably iodide.

It will be apparent that the above-described reaction lends itself readily to continuous operation in which the reactants and catalyst are continuously supplied to the appropriate reaction zone and the reaction mixture continuously distilled to separate the volatile organic constituents and to provide a net product consisting essentially of carboxylic ester with the other organic components being recycled and, in a liquid-phase reaction a residual catalyst containing fraction also being recycled.

It will also be apparent that the catalytic reaction involved in the process of the invention can be carried out in the vapor phase, if desired, by appropriate control of the total pressure in relation to the temperature so that the reactants are in vapor form when in contact with the catalyst. In the case of vapor-phase operation, and in the case of liquid-phase operation, if desired, catalyst components may be supported i.e., they may be dispersed on a carrier of conventional type such as alumina, silica, silicon carbide, zirconia, carbon, bauxite, attapulgus clay, and the like. The catalyst components can be applied to the carriers in conventional manner, e.g., by impregnation of the carrier with a solution of the catalyst component. Concentrations upon the carrier may vary widely, e.g., 0.01 weight percent to 10 weight percent, or higher. Typical operating conditions for vapor-phase operation are a temperature of 100° to 350° C., preferably 150° to 275° C. and most preferably 175° to 255° C., a pressure of 1 to 5,000 p.s.i.a., preferably 50 to 1,500 p.s.i.a. and most preferably 150 to 500 p.s.i.a., with space velocities of 50 to 10,000 hr.$^{-1}$, preferably 200 to 6,000 hr.$^{-1}$ and most preferably 500 to 4,000 hr.$^{-1}$ (STP). In the case of a supported catalyst, the iodide component is included with the reactants and not on the support.

Because the process of this invention involves relatively low pressures and relatively low concentrations of halide component, it is, as previously mentioned, possible to operate under boiling reactor conditions, i.e., in a carbonylation zone wherein the pressure and temperature are selected so that the liquid reaction medium is under continuously boiling conditions and the reaction mixture effluent is withdrawn as a vapor, which is then condensed and freely distilled to separate it into its components for removal or recycling. In this embodiment, the catalyst remains in the reaction zone at all times since it is relatively non-volatile. In a particularly favorable manner of operating under boiling reactor conditions, the alcohol is fed continuously to the reaction zone and the pressure is selected so that the desired ester is vaporized and removed from the reaction zone substantially as it is formed for subsequent recovery from the vaporous effluent.

The following examples will serve to provide a fuller understanding of the invention, but it is to be understood that they are given for illustrative purposes only, and are not to be construed as limitative of the invention. In the examples, all parts and percentages are by weight, unless otherwise indicated.

EXAMPLE 1

In this example, a magnetically-stirred Hastelloy Parr bomb with a glass liner is employed as the reaction vessel. The bomb is charged with ethyl propionate (150 parts), ethyl iodide (50 parts), nickel iodide (8 parts) plus molybdenum hexacarbonyl (15 parts) as co-catalyst, triphenylphosphine (20 parts) and methanol (100 parts), is swept out with argon and is pressured to 50 psig with hydrogen and then to 400 psig with carbon monoxide. The vessel is heated to 180° C. with stirring. Then the vessel is charged with ethylene to bring the pressure to 900 psig. The pressure is maintained at 900 psig by recharging carbon monoxide and ethylene in equal amounts when needed and the temperature is maintained at 180° C. After 2 hours reaction, G. C. analysis of the reaction effluent shows it to contain 83 parts methyl propionate. All of the ethyl propionate introduced as solvent is recovered.

EXAMPLE 2

Using a reaction vessel as described in Example 1, the bomb is charged with ethyl propionate (150 parts), ethyl iodide (50 parts), methanol (100 parts), nickel iodide (8 parts), molybdenum hexacarbonyl (15 parts) and pyridine (7 parts). The bomb is then swept out with argon, pressured to 50 psig with hydrogen and to 400 psig with carbon monoxide. The vessel is heated to 175° C. and pressured to 950 psig with ethylene. The pressure is maintained at 950 psig by charging a 1:1 mixture of carbon monoxide and ethylene as needed and the temperature is maintained at 175° C. After 3 hours of reaction, G. C. analysis of the reaction mixture shows it to contain 19.7% methyl propionate (66 parts). All of the ethyl propionate initially charged is recovered.

EXAMPLE 3

Example 1 is repeated except that the nickel iodide is replaced by an equivalent amount of nickel carbonyl. It is found that 92 parts of methyl propionate are formed, all ethyl propionate being recovered.

EXAMPLE 4

Example 1 is again repeated except that the methyl iodide is replaced by an equivalent amount of bis-triphenylphosphine nickel carbonyl and the ethyl iodide is replaced by an equivalent amount of ethyl bromide. It is found that 75 parts of methyl propionate are formed, all ethyl propionate being recovered.

EXAMPLE 5

Example 4 is repeated but the ethyl bromide is replaced with an equivalent quantity of chloroethane. It is found that 76 parts of methyl propionate are formed, all ethyl propionate in the charge being recovered.

EXAMPLE 6

Example 1 is repeated but the molybdenum hexacarbonyl is replaced by a corresponding quantity of tungsten hexacarbonyl. Fifty-nine parts of methyl propionate are formed, all ethyl propionate initially charged being recovered.

EXAMPLE 7

Example 1 is again repeated but the triphenylphosphine is replaced with an equivalent amount of triphenylphosphine. It is found that 102 parts of methyl propionate are formed, all ethyl propionate being recovered.

EXAMPLE 8

Example 1 is repeated once again but in this example the triphenylphosphine is replaced with 7 parts 2-picoline. Seventy-three parts methyl propionate are formed, all of the ethyl propionate being recovered.

EXAMPLE 9

The reactor used in this example is a magnetically-stirred pressure vessel provided with a glass liner and adapted to function as a boiling reactor, i.e., a reactor in which the liquid reaction mixture is maintained in a boiling state and the reactor effluent is in the vapor phase. The vessel is charged with 250 parts propionic acid as solvent, 50 parts ethyl iodide, 3 parts nickel iodide (NiI$_2$.6H$_2$O), 6 parts molybdenum hexacarbonyl and 30 parts triphenylphosphine. The vessel is swept out with argon and is pressured to 240 psig with carbon monoxide containing 5% hydrogen. Then the vessel is heated to 177° C. with stirring and is pressured to 600 psig by means of a 1:1 mixture of ethylene and carbon monoxide, the carbon monoxide containing 5% hydrogen. The gas mixture is allowed to flow through the reactor at the rate of 100 liters per hour. The effluent vapors are cooled to room temperature and the portion which condenses is collected periodically. A mixture of methanol and ethyl iodide is continuously pumped into the reactor. After steady-state operation has been achieved, liquid feed is continued at the rate of 22.7 parts per hour methanol and 2.2 parts per hour ethyl iodide. The rate of liquid effluent is 74.5 parts per hour. The effluent is found to contain, on average, 4.75 parts methanol, 2.05 parts ethyl iodide and 49.1 parts methyl propionate. All of the propionic acid initially charged as solvent is recovered.

What is claimed is:

1. In a process for the preparation of a carboxylic acid ester by reacting an olefin with carbon monoxide in the presence of an alcohol, the improvement which comprises carrying out said reaction in the presence of a catalyst comprising a molybdenum-nickel or a tungsten-nickel co-catalyst component, in the presence of a halide and in the presence of a promoter comprising an organo-phosphorus compound or an organo-nitrogen compound wherein the phosphorus and nitrogen are trivalent.

2. A process as defined in claim 1, wherein the co-catalyst component comprises molybdenum-nickel.

3. A process as defined in claim 1, wherein the promoter is a phosphine.

4. A process as defined in claim 3, wherein the co-catalyst comprises molybdenum-nickel and the promoter is a phosphine.

* * * * *